United States Patent
Ohren et al.

(10) Patent No.: US 9,594,230 B2
(45) Date of Patent: Mar. 14, 2017

(54) ON-AXIS FOCUS SENSOR AND METHOD

(71) Applicant: Rudolph Technologies, Inc., Flanders, NJ (US)

(72) Inventors: Dennis L. Ohren, Victoria, MN (US); Christopher J. Voges, Eden Prairie, MN (US); Andrew E. Rotering, Minneapolis, MN (US)

(73) Assignee: Rudolph Technologies, Inc., Wilmington, MA (US)

( * ) Notice: Subject to any disclaimer, the term of this patent is extended or adjusted under 35 U.S.C. 154(b) by 94 days.

(21) Appl. No.: 14/367,564

(22) PCT Filed: Dec. 20, 2012

(86) PCT No.: PCT/US2012/071030
§ 371 (c)(1),
(2) Date: Jun. 20, 2014

(87) PCT Pub. No.: WO2013/096660
PCT Pub. Date: Jun. 27, 2013

(65) Prior Publication Data
US 2014/0368635 A1 Dec. 18, 2014

Related U.S. Application Data

(60) Provisional application No. 61/580,028, filed on Dec. 23, 2011.

(51) Int. Cl.
*G02B 7/28* (2006.01)
*G01N 21/84* (2006.01)
(Continued)

(52) U.S. Cl.
CPC ............... *G02B 7/28* (2013.01); *G01B 11/00* (2013.01); *G01B 11/026* (2013.01);
(Continued)

(58) Field of Classification Search
CPC ...... G02B 7/28; H04N 5/23212; H04N 5/217; H04N 7/18; G01N 21/84; G01N 2201/127;
(Continued)

(56) References Cited

U.S. PATENT DOCUMENTS

| 4,891,529 | A | * | 1/1990 | Braun ................ G01B 11/00 250/559.19 |
| 5,543,918 | A | * | 8/1996 | Abraham ........... G01B 11/026 356/609 |

(Continued)

FOREIGN PATENT DOCUMENTS

| JP | H08178623 | | 7/1996 | |
| JP | H08178623 A | * | 12/1996 | ............ G01B 11/02 |
| JP | H08334309 | | 12/1996 | |
| JP | H08178623 | * | 3/2004 | ........... G01B 11/022 |
| JP | 2006184303 | | 7/2006 | |

OTHER PUBLICATIONS

The Search Report for Application No. PCT/US2012/071030 mailed Apr. 25, 2013.

*Primary Examiner* — Chikaodili E Anyikire
*Assistant Examiner* — Dramos I Kalapodas
(74) *Attorney, Agent, or Firm* — Dicke, Billig & Czaja, PLLC

(57) ABSTRACT

A focus height sensor in an optical system for inspection of semiconductor devices includes a sensor beam source that emits a beam of electromagnetic radiation. A reflector receives the beam of electromagnetic radiation from the sensor beam source and directs the beam toward a surface of a semiconductor device positioned within a field of view of the optical system. The reflector is positioned to receive at least a portion of the beam back from the surface of the semiconductor device to direct the returned beam to a sensor. The sensor receives the returned beam and outputs a (Continued)

signal correlating to a position of the surface within the field of view along an optical axis of the optical system.

11 Claims, 2 Drawing Sheets

(51) Int. Cl.
*G01B 11/00* (2006.01)
*G01B 11/02* (2006.01)
*G01B 11/06* (2006.01)
*H04N 5/232* (2006.01)
*G01N 21/95* (2006.01)

(52) U.S. Cl.
CPC ......... *G01B 11/0608* (2013.01); *G01N 21/84* (2013.01); *H04N 5/23212* (2013.01); *G01N 21/9501* (2013.01); *G01N 2201/127* (2013.01)

(58) Field of Classification Search
CPC ............... G01N 21/9501; G01N 21/88; G01B 11/0608; G01B 11/026; G01B 11/00; G01C 5/00
USPC ............. 250/560, 223; 356/376; 413/12, 66; 358/107
See application file for complete search history.

(56) References Cited

U.S. PATENT DOCUMENTS

| | | | | |
|---|---|---|---|---|
| 6,177,998 | B1* | 1/2001 | Svetkoff | G01B 11/026 250/559.23 |
| 6,521,889 | B1* | 2/2003 | Ina | G01N 21/88 356/237.3 |
| 6,879,403 | B2* | 4/2005 | Freifeld | G01B 11/024 356/237.4 |
| 6,954,267 | B2* | 10/2005 | Abraham | G01F 23/284 356/237.2 |
| 7,924,435 | B2* | 4/2011 | Colonna De Lega | G01B 9/02057 356/511 |
| 2002/0001403 | A1* | 1/2002 | Kikuchi | G01N 21/9501 382/145 |
| 2006/0038980 | A1* | 2/2006 | Naka | G01N 21/65 356/73 |
| 2008/0266575 | A1* | 10/2008 | Gaitas | B82Y 35/00 356/600 |
| 2010/0171955 | A1* | 7/2010 | Suga | G01B 11/026 356/364 |
| 2011/0127406 | A1 | 6/2011 | Sase | |
| 2012/0327208 | A1* | 12/2012 | Higaki | G02B 21/365 348/79 |

* cited by examiner

ON-AXIS FOCUS SENSOR AND METHOD

CROSS REFERENCE TO RELATED APPLICATION

This Utility Patent Application claims priority under 35 U.S.C. §371 to International Application Serial No. PCT/US12/71030, filed Dec. 20, 2012, which claims the benefit of U.S. Patent Application No. 61/580,028, filed Dec. 23, 2011; which are both incorporated herein by reference.

BACKGROUND

In high resolution optical inspection imaging systems, it is important to ensure that an object plane of the optical system remains substantially in focus with respect to an image plane of the optical system. Doing so ensures that the resulting images are of sufficient quality for inspection purposes.

Ensuring that an optical system remains in focus can be accomplished in a number of ways. One way is to use an auto-focus technique in which a series of images at different focal positions are captured and then assessed to identify the optimal focal position. This approach is well understood, but is very slow as it requires multiple images at each position at which one desires to find a focal position.

Another technique is to use a height sensor such as a laser triangulation system or a capacitive height sensor to determine the height of a surface that is being imaged. Once the height has been determined, the optical system may be adjusted to ensure the object plane of the optical system is placed at the surface of the object being imaged. Such height sensors may be positioned to determine the height of the substrate within the field of view of the optical system or at a lateral offset from the field of view.

Systems that capture height at a lateral offset implement a mathematical transform to ensure that the height measured may be used at the field of view for focal positioning. It may be preferable to avoid the need for implementing such a transform and so it is often desirable to use a height sensor, as mentioned above, that determines the height of the object being imaged within the field of view. One such system uses a laser triangulation type sensor in which a measurement beam is incident on the object being imaged within the field of view. Given the extremely tight dimensional tolerances inherent in a high resolution imaging system, this type of system requires specially arranged objectives that have one or more optical components of the height sensor, either an optical element or a portion of an optical path, formed therein. The specialized nature of these systems reduces their flexibility, increases their expense, and makes it difficult to modify the system to capture images at different resolutions.

Another type of height sensor that measures surface height of an object being imaged at the field of view of an imaging system is adapted to operate within the actual optical path of the imaging system. By directing a measurement beam, such as the beam of a laser triangulation sensor, through a lens of the optical system onto the object being imaged within the field of view can provide an indication of the height of object. Such measurement systems require direct integration with an imaging system, which can be both complex and quite expensive. Further, light from a measurement beam can interfere with an imaging process.

Accordingly, there is a need to provide a focus height sensor that is inexpensive, simple to install and maintain, and which can measure the height of an object at a field of view of an imaging system.

SUMMARY

One aspect disclosed herein is a focus height sensor in an optical system for inspection of semiconductor devices. The focus height sensor includes a sensor beam source that emits a beam of electromagnetic radiation. A reflector receives the beam of electromagnetic radiation from the sensor beam source and directs the beam toward a surface of a semiconductor device positioned within a field of view of the optical system. The reflector is positioned to receive at least a portion of the beam back from the surface of the semiconductor device to direct the returned beam to a sensor. The sensor receives the returned beam and outputs a signal correlating to a position of the surface within the field of view along an optical axis of the optical system.

In another aspect, a method of capturing images of a semiconductor substrate is also disclosed that includes positioning selectively a reflector in an operative position to direct a sensor beam toward a semiconductor substrate. The reflector receives from the semiconductor substrate at least a portion of the sensor beam and directs it to a sensor which outputs a signal to a controller correlated to a position of a surface of the semiconductor substrate. A focusing mechanism is controlled to position an object plane of the optical system at substantially the same position output by the sensor and report it to the controller. An objective is positioned selectively in an operative position to capture an image of the semiconductor substrate.

In another aspect, a method of capturing images of a semiconductor substrate includes actuating a turret of an optical system to place a reflector in an operative position to direct a measuring beam onto a surface of a semiconductor substrate. At least a portion of the measuring beam is returned from the semiconductor substrate to a sensor to determine a height of the semiconductor substrate. A focusing mechanism of the optical system is actuated to focus the optical system at the height determined by the sensor. The turret is actuated to place an objective in an operative position in order to capture an image of the semiconductor substrate at substantially the location at which the height of the semiconductor substrate was measured. An image of the semiconductor substrate is captured using the optical system.

In yet a further aspect, a method of calibrating a position of an optical system is disclosed. The method includes driving an optical system focusing mechanism to a predetermined location. The position of the optical system is measured using a height sensor and the position of the optical system is measured using an autofocus height process conducted by the optical system. The respective position information is compared to determine if there is acceptable agreement between the data. Where acceptable agreement exists, an imaging process is continued or started. Where acceptable agreement does not exist, the height data obtained from one of the height sensor and the optical system is modified to insure acceptable agreement therebetween.

DETAILED DESCRIPTION

Figure 1:
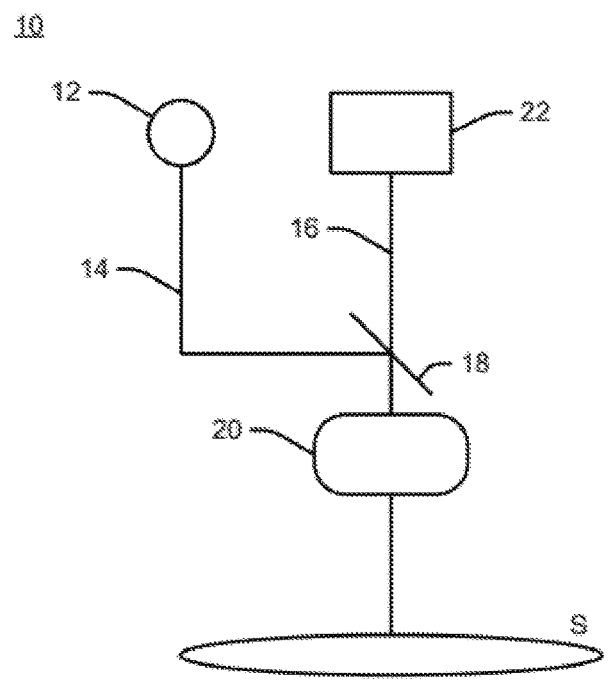
FIG. 1 is a schematic view of an exemplary imaging system.

Concepts presented herein relate to a height sensor that is adapted for use with an imaging system for inspecting or measuring semiconductor substrates. FIG. 1 illustrates schematically an exemplary imaging or optical system 10 that may incorporate a height sensor. It is to be understood that other optical systems may also be adapted to incorporate the present invention and that those skilled in the art will be able to make such adaptations on the basis of the present specification.

Figure 2:
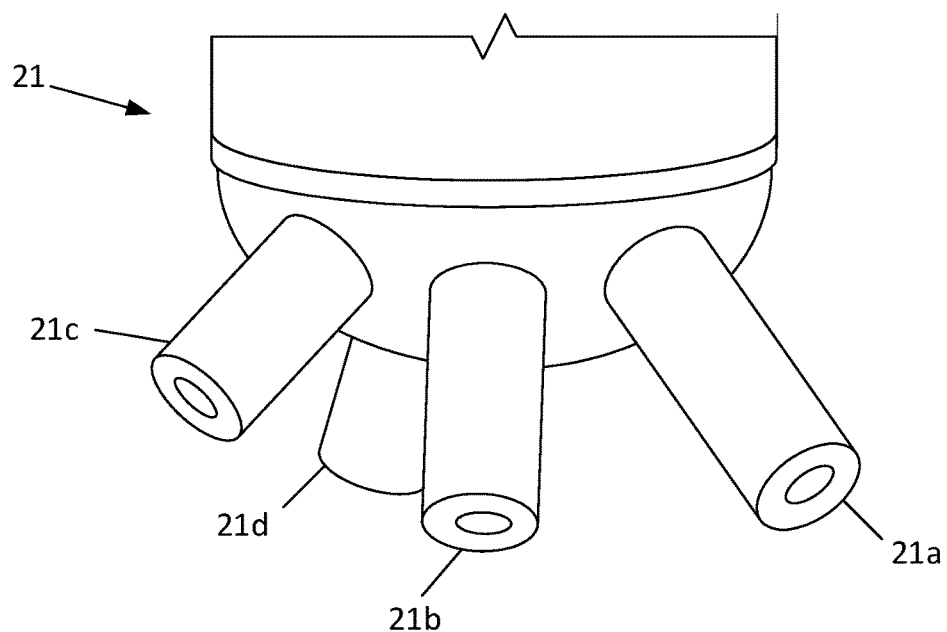
FIG. 2 is an isometric view of a turret employing multiple objectives having different imaging resolutions.

The system 10 shown in FIG. 1 includes a source of electromagnetic radiation, herein embodied as an illuminator 12 that emits light along path 14. Light traveling on path 14 is coupled onto an optical axis 16 by means of a coupling element 18, which is in some embodiments a beam splitter, dichroic mirror, or a fiber optic device. Light traveling along optical axis 16 passes through relay optics 20 and onto a substrate S that is being imaged. The relay optics 20 are of a type well known to those skilled in the art and may comprise one or more objectives in a turret for selecting different imaging resolutions. An example turret 21 is shown in FIG. 2, having objectives 21a-21d of different resolutions. The various resolutions are typically referred to as 1×, 2×, 5× and the like. These and similar designations relating to other imaging resolutions are well known to those skilled in the art.

During inspection, light from the illuminator 12 is incident upon the substrate S and at least a portion of this incident light is returned from the substrate S along the optical path 16 to a camera 22 for capturing an image of the substrate S. Note that the camera 22 includes a sensor (not shown) which may be a CCD, CMOS or other suitable light sensitive medium capable of capturing an image of the substrate S. The sensor of the camera 22 defines an image plane of the optical system 10 that is conjugate with an object plane that is defined by the relay optics 20 in a well-known manner. When the object plane of the optical system is positioned coincident or substantially coincident with the surface of the substrate S this is being imaged, the optical system is said to be focused on the substrate S. Note that the lateral extent that the sensor the camera can "see" of the substrate S is referred to as the field of view of the optical system.

Focusing an optical system 10 can be accomplished in a number of ways using a focusing mechanism, each depending on the specific nature of the optical system itself. Where the object plane of the optical system 10 is fixed in space with respect to the image plane, focusing may be accomplished by moving the entire optical system 10 so that in capturing an image, the object plane is located at the surface of the object being imaged or at least near enough to provide a user-defined level of image quality or resolution. Where the image plane is fixed in space and the object plane may be moved with respect thereto, typically by modifying the relay optics (e.g., by rotating a turret), proper focus can be obtained by moving some or all of the relay optics. Other methods may be known to those skilled in the art.

Figure 3:
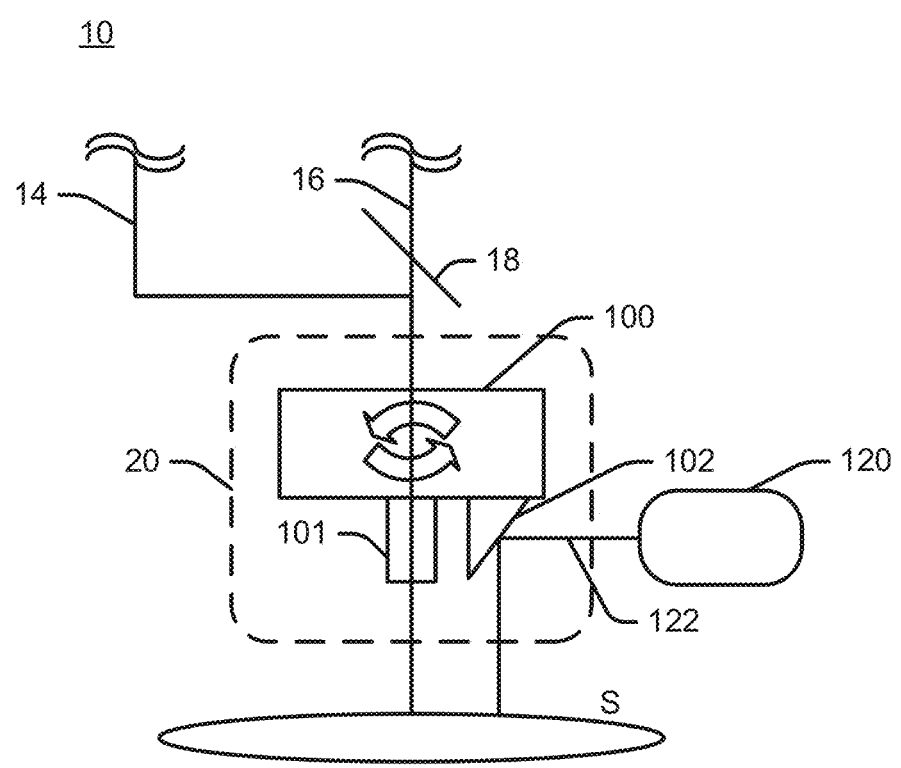
FIG. 3 is a schematic close-up view of a portion of the imaging system of FIG. 1 employing a height sensor.

As illustrated in FIG. 3, in an embodiment of system 10 that includes an objective turret or changer 100 as part of the relay optics 20, a reflector 102 may be included in addition to an objective 101. The changes 100 can be utilized to selectively position the reflector 102 in an operative position to direct a beam toward substrate S. As discussed below, a sensor 120 receives a beam 122 from the substrate S and outputs a signal correlated to a position (e.g., a height) of the substrate S. In one embodiment, the position is calculated as a distance between the relay optics 20 and the substrate S. In some embodiments, the optical system 10 can be adjusted using a focusing mechanism to position an object plane at the same position that is output. Furthermore, an objective can be selectively positioned to capture an image of the substrate based on the position. In a further embodiment, the objective 101 and the reflector 102 are coupled with a turret and the turret is actuated to selectively place the objective 101 and reflector 102 in an operative position.

Note that the changer 100 switches the objective 101 with the reflector 102 as needed such that both the objective and the reflector may optically address substantially the same field of view associated with optical axis 16. FIG. 3 illustrates the reflector 102 and objective 101 as optically addressing substantially different fields of view on the substrate S for simplicity's sake only. In a simple embodiment the changer 100 may include one objective 101 for imaging a field of view and a reflector 102. Where the objective 101 facilitates the imaging of a substrate or object, the reflector 102 directs a measurement beam to the field of view of the objective, keeping in mind that in this arrangement only one of the objective 101 and the reflector 102 are in use at any given time.

In other embodiments, a changer 100 may include more than one objective in addition to a reflector 102. In yet other embodiments no changer 100 is present on optical system 10. Rather, a coupling mechanism allows a user to rapidly attach an objective or reflector to the optical system 10. Such a coupling mechanism may be a threaded coupling structure, a ball and detent device or even a friction fit type of connector. In this way, a user of the optical system 10 can rapidly modify the relay optics 20 to switch between an imaging mode, in which an image is captured through relay optics 20, and a height determination mode in which a surface height or profile of substrate is determined using a reflector in conjunction with a focus height sensor 120.

Determining a surface height or profile may be accomplished in a number of ways. In one embodiment a sensor 120 is a sensor beam source configured to generate a measuring beam 122 and positioned such that a measuring beam 122 is directed from the sensor 120 to the reflector 102 and thence to the surface of the substrate S substantially at the intersection of the optical axis 16 of the optical system 10 with the substrate S. At least a portion of the measuring beam 122 is returned from the surface of the substrate S to the reflector 102 and thence back to the sensor 120. The measuring beam 122 causes the sensor 120 to output a signal that is correlated with a height or position of the substrate S at the point where the measuring beam 122 is incident. Preferably the height or position of the substrate substantially at the optical axis 16 of the system 10 or at least within the field of view of the optical system 10 is obtained. Note that in some embodiments the sensor 120 may be coupled directly to the optical system 10 and will travel therewith as focus positions/heights are modified. In other embodiments the height sensor is mounted independently from the optical system 10.

The reflector 102 may be a simple mirror angled so as to direct a measuring beam to and from the sensor 120 and the substrate S. In some embodiments the reflector 102 is fixed and has no optical power. In other embodiments the reflector 102 may have some optical power to focus the measuring beam. The reflector or some component of a relay system described herein as the reflector may have an oscillator associated therewith to sweep or scan the measuring beam 122 over an area. Where no such oscillator is included, the beam 122 would essentially measure a point and by scanning the substrate S beneath the point, lines or areas may be measured. A suitable oscillatory device may be a voice coil, a piezoelectric actuator, an acousto-optic modulator (AOM) or an electro-optic modulator (EOM). The reflector may also be a set of optical elements arranged so as to selectively direct a measuring beam 122 or radiation to/from a substrate and sensor, preferably within a field of view of an optical system. In embodiments of this latter type, some of the optical elements may be included on changer 100 and others may be mounted separate from the changer 100. In various embodiments, the reflector 102 may direct measuring beams or radiation through the air or may couple such beams at least partially through fiber optic type elements.

In yet other embodiments, the sensor 120 may have substantially the same form factor as an optical objective coupled to the changer such that no reflection of light to a sensor apart from the changer will be necessary. In this embodiment, as well as for other types of embodiments, care must be taken to ensure that the requisite electrical and/or optical connections are made in such a way as to avoid interfering with the operation of the changer. For example, an electrical connection between a height sensor having an objective form factor and a controller using an electrical slip connection between the changer and the remainder of the optical system (not shown). Alternatively, an optical fiber connection between a reflector and a sensor may be made using a fiber optical cable having sufficient slack to allow for a useful degree of rotation or translation of the changer, thereby facilitating a switch between objectives or between an objective and the reflector.

In some embodiments only a small number of points are obtained over the entire surface of a substrate S. In these embodiments it is common for the few data points that are obtained to be used to model or extrapolate the height of all or a selected portion of the substrate S where height data was not obtained, i.e. are used to determine the height of a surface of a substrate within a field of view of an optical system where height data was not captured. In some other embodiments, a large number of sample data points are captured to create a data base or model that is much more representational of the profile or height of the surface of the substrate S. In this instance, the modeling or extrapolation that is required allows for a higher resolution determination than where fewer data points were obtained. In yet other embodiments only a single height measurement is obtained. In each case, the specificity of the height information is correlated to the resolution requirements of the imaging system 10. For example, where high resolution images are required of an optical system 10 it may be desirable to obtain a height data point in or adjacent to a majority of the fields of view that would be captured by the optical system 10 during operation. As a general rule, the higher the resolution of the optical system 10, the more discrete data points will be necessary for ascertaining a height or profile of the substrate S that will be imaged. As an additional example, where low resolution images are needed or where there is a high degree of confidence with respect to the overall surface height or position (e.g. as a result of previous measurements or operations performed on the substrate such as lapping) then fewer data points are required.

In another embodiment, a reflector and height measurement sensor may be also be used for metrology or inspection of a substrate S or portions thereof. Any height measurement sensor that may take the form of an objective or which can be optically directed by a reflector to a substrate and vice versa as described above can be used to obtain a surface profile of a substrate S or features on the substrate S such as bond pads, solder bumps, probe marks and other three dimensional features. In addition to laser triangulation sensors, one can use a confocal sensor (scanning or chromatic aberration types). In such embodiments, the substrate S is moved beneath the sensor to address selected points, lines, areas or even substantially the entire surface of the substrate S to the sensor. Such metrology data may also be used for focusing an optical system 10. Two suitable types of sensors are available from Keyance Corporation of America located in Chicago, Ill. One such sensor is a one dimensional laser sensor (LK Series of laser displacement sensors). Another such sensor is a two dimensional laser displacement sensor such as the LJ-G series of sensors. Other types interferometric and/or spectral sensors for determining height and/or displacement may be used in conjunction with a reflector 120 to determine a height or profile of a substrate S as part of the present invention.

In addition to focusing and metrology/inspection, an optical system 10 may be periodically calibrated using a height sensor and a reflector to ensure the proper operation of the optical system 10. Where a changer 100 has inherent mechanical variation, a reflector can be used to verify the position or operation of an objective or other optical element of all or part of the relay optics referenced above. Similarly, where the handling mechanisms (such as a top plate or chuck on an X/Y or X/Y/Z or X/Y/Theta stage (not shown)) that support and move a substrate S with respect to an optical system 10 are subject to variability, the height sensor may be used to verify the operation of the handling mechanism.

In one embodiment a reflector is used with a height sensor to obtain at least one height measurement on a substrate S. Subsequently, the optical system 10 conducts an auto focus or other focusing operation at the same position at which the height measurement was taken. The height information obtained from the respective systems or sensors are compared to determine whether there is good agreement therebetween. If so, subsequent imaging operations (or other types of operations requiring good focus) may commence or continue. If not, a measurement from one of the optical system 10 or height sensor is modified so that there is good agreement therebetween. While not strictly necessary, after such an adjustment is made, it is often desirable to conduct a subsequent calibration procedure to ensure the corrections are, in fact, correct. Where good agreement between the data obtained from the optical system 10 and the height sensor does not exist, various error checking routines may be conducted to determine and remedy any errors that have led to the lack of agreement in measured data. For example, linear or rotary encoders used in conjunction with linear or rotary actuators or drives may be zeroed or otherwise calibrated or checked to ensure that they are reporting the appropriate data. In one embodiment, structure mounted on a stage is driven (carefully) into contact with a fixed stop of known position. Upon determining that contact has been made, the actual position reported by an encoder is compared with the nominal position of the stop to ensure that there is agreement therebetween. Where there is no agreement, the encoder output is zeroed or otherwise modified such that its output matches the location of the fixed location stop. This calibration method may be used with linear or rotary stages.

In one embodiment, a chuck or top plate mounted on at least one of a rotary and/or one or more linear stages is provided with at least one optical target in its upper surface. One form of optical target that may be used is one or more figures such as a cruciform figure that is positioned at a known location on the top plate, though any figure having a known shape and position may suffice. A height sensor working in conjunction with a reflector may capture a height measurement of the top plate at the optical target. Subsequently, the optical system may conduct an autofocus routine at the optical target on the top plate to determine an optimal height for the focus plane of the optical system 10. The measured height (obtained from the height sensor) and the position of the focal plane of the optical system 10 as determined using an autofocus routine are normalized such that the focal plane of the optical system is coincident with the surface of the substrate S being imaged. This normalization or calibration is carried out by a controller such as a host computer system that is coupled to both the optical system 10 and the height sensor. As those skilled in the art will appreciate, the controller will coordinate the movement of a substrate (or in some instances movement of the optical system 10) relative to the optical system 10 to facilitate imaging operations. An example of this coordination is described in U.S. Pat. No. 7,729,528 which is owned jointly with the present invention. Other implementations are also contemplated and accordingly, the foregoing description is not intended to limit a range of applications to which the invention as claimed below may be addressed.

Although the present invention has been described with reference to preferred embodiments, workers skilled in the art will recognize that changes can be made in form and detail without departing from the spirit and scope of the present invention.

What is claimed is:

1. An optical system for inspection of semiconductor devices, the optical system comprising:
    a focus height sensor including:
        a sensor beam source that emits a beam of electromagnetic radiation;
        a sensor; and,
        a reflector for receiving the beam of electromagnetic radiation from the sensor beam source and directing said beam toward a surface of a semiconductor device that is positioned within a field of view of the optical system, the reflector also being positioned and configured to receive at least a portion of said beam back from the surface of the semiconductor device to direct the returned beam to the sensor;
        wherein the sensor is configured to receive the returned beam from the reflector and output a signal correlating to a position of the surface within the field of view along an optical axis of the optical system; and
    a turret, wherein the reflector is mounted in the turret, and further wherein the turret is configured to be actuated to selectively place and remove the reflector from an operative position in which the reflector directs the beam toward the surface and receives at least a portion of the beam back from the surface.

2. The optical system of claim 1 further comprising:
    a focusing mechanism coupled to the optical system for moving an object plane of the optical system based at least in part on the signal provided from the sensor.

3. The optical system of claim 1 wherein the focus height sensor is one of a laser triangulation sensor, a chromatic confocal sensor and a scanning confocal sensor.

4. The optical system of claim 1 wherein the turret is moveable between a first position in which an objective coupled to the turret is positioned substantially coaxially with an optical axis of the optical system and a second position in which the reflector is positioned to direct the beam to the surface of the substrate and to direct a beam returned from the surface to the sensor.

5. A method of capturing images of a semiconductor substrate comprising:
    actuating a turret of an optical system to position selectively a reflector in an operative position;
    directing a sensor beam toward a semiconductor substrate via the reflector;
    receiving at the reflector at least a portion of the sensor beam returned from the semiconductor substrate;
    directing the returned beam to a sensor via the reflector;
    operating the sensor to output a signal to a controller correlated to a position of a surface of the semiconductor substrate based upon the returned beam;
    controlling a focusing mechanism of an optical system to position an object plane of the optical system at substantially the same position output by the sensor and reported to the controller; and,
    positioning selectively an objective of an optical system in an operative position to capture an image of the semiconductor substrate.

6. A method of capturing images of a semiconductor substrate comprising:
    actuating a turret of an optical system to place a reflector in an operative position to direct a measuring beam onto a surface of a semiconductor substrate and to return at least a portion of the measuring beam from the semiconductor surface to a sensor to determine a height of the semiconductor substrate;
    actuating a focusing mechanism of the optical system to focus the optical system at the height determined by the sensor;
    actuating the turret to place an objective in an operative position to capture an image of the semiconductor substrate at substantially the location at which the height of the semiconductor substrate was measured; and,
    capturing an image of the semiconductor substrate using the optical system.

7. The method of claim 6 wherein only one of the reflector and the objective is in its operative position at any given time.

8. The method of claim 6 further comprising conducting an image processing step on the captured image to identify a defect of the semiconductor substrate, if any exist.

9. The method of claim 6 further comprising capturing height information over substantially an entire region to determine a height profile of the region.

10. The method of claim 6 wherein the sensor is selected from a group consisting of a laser triangulation sensor, a chromatic confocal sensor, and a scanning confocal sensor.

11. The method of claim 6 further comprising normalizing position data obtained from an autofocus process conducted on the optical system with position data obtained from the sensor.

* * * * *